United States Patent [19]
Underwood et al.

[11] Patent Number: 6,035,476
[45] Date of Patent: Mar. 14, 2000

[54] BRUSHHEAD FOR A TOOTHBRUSH

[75] Inventors: Kevin T. Underwood, Issaquah; Stephen M. Meginniss, III, Seattle, both of Wash.; Steven R. Henrikson, Morristown, Tenn.

[73] Assignee: Optiva Corporation, Snoqualmie, Wash.

[21] Appl. No.: 09/335,232

[22] Filed: Jun. 17, 1999

Related U.S. Application Data

[63] Continuation-in-part of application No. 09/150,877, Sep. 10, 1998.

[51] Int. Cl.[7] ............................. A46B 9/04; A46B 13/02; A61C 17/22
[52] U.S. Cl. .................... 15/22.1; 15/167.1; 15/191.1; 15/195; 15/DIG. 5; D4/101; D4/104
[58] Field of Search ................... 15/22.1, 167.1, 15/191.1, 195, DIG. 5; D4/101, 104

[56] References Cited

U.S. PATENT DOCUMENTS

| | | | |
|---|---|---|---|
| D. 397,251 | 8/1998 | Eguchi et al. | D4/101 |
| 1,059,426 | 4/1913 | Barnes | 15/167.1 |
| 1,657,450 | 1/1928 | Barnes | 15/167.1 |
| 1,943,225 | 1/1934 | McIntyre | 15/167.1 |
| 2,273,717 | 2/1942 | Millard et al. | 15/167.1 |
| 3,840,932 | 10/1974 | Balamuth et al. | 15/167.1 |
| 4,268,933 | 5/1981 | Papas | 15/167.1 |
| 4,617,695 | 10/1986 | Amos et al. | 15/195 |
| 4,672,706 | 6/1987 | Hill | 15/167.1 |
| 5,305,492 | 4/1994 | Giuliani et al. | 15/176.1 |
| 5,378,153 | 1/1995 | Giuliani et al. | 433/216 |
| 5,459,898 | 10/1995 | Bacolot | 15/106 |
| 5,511,275 | 4/1996 | Volpenhein et al. | 15/167.1 |
| 5,687,446 | 11/1997 | Chen et al. | 15/195 |
| 5,735,011 | 4/1998 | Asher | 15/167.1 |
| 5,896,614 | 4/1999 | Flewitt | 15/167.1 |

FOREIGN PATENT DOCUMENTS

| | | | |
|---|---|---|---|
| 695325 | 9/1930 | France | 15/167.1 |

OTHER PUBLICATIONS

Butler toothbruch (photocopy of ad showing toothbrush configuration).
Periodontal Diseases, 2nd Ed., Lea & Febriger 1990, pp. 356–358.
Periodontal Therapy, 5th Ed., C.V. Mosby Company 1974, pp. 429–432.
Jordan V toothbrush (photography of packaging showing brush configuration).
Zahoransky toothbrush (pictures of actual toothbrush).

*Primary Examiner*—Mark Spisich
*Attorney, Agent, or Firm*—Jensen & Puntigam

[57] ABSTRACT

A brushhead for a toothbrush having a particular bristle configuration which includes a plurality of bristle tufts arranged in three columns and nine rows, wherein the distal end two adjacent rows and the proximal end two adjacent rows and an intermediate row have longer bristles than the remaining bristle tuft rows. The distal, intermediate and proximal bristle tuft rows all have pointed tips (in the lateral direction) and beveled outside edges at the top portion thereof. The shorter bristle tuft rows also have beveled outside edges. The shorter bristle tuft rows between the distal and intermediate rows have angled top surfaces in addition to the beveled outside edges.

40 Claims, 5 Drawing Sheets

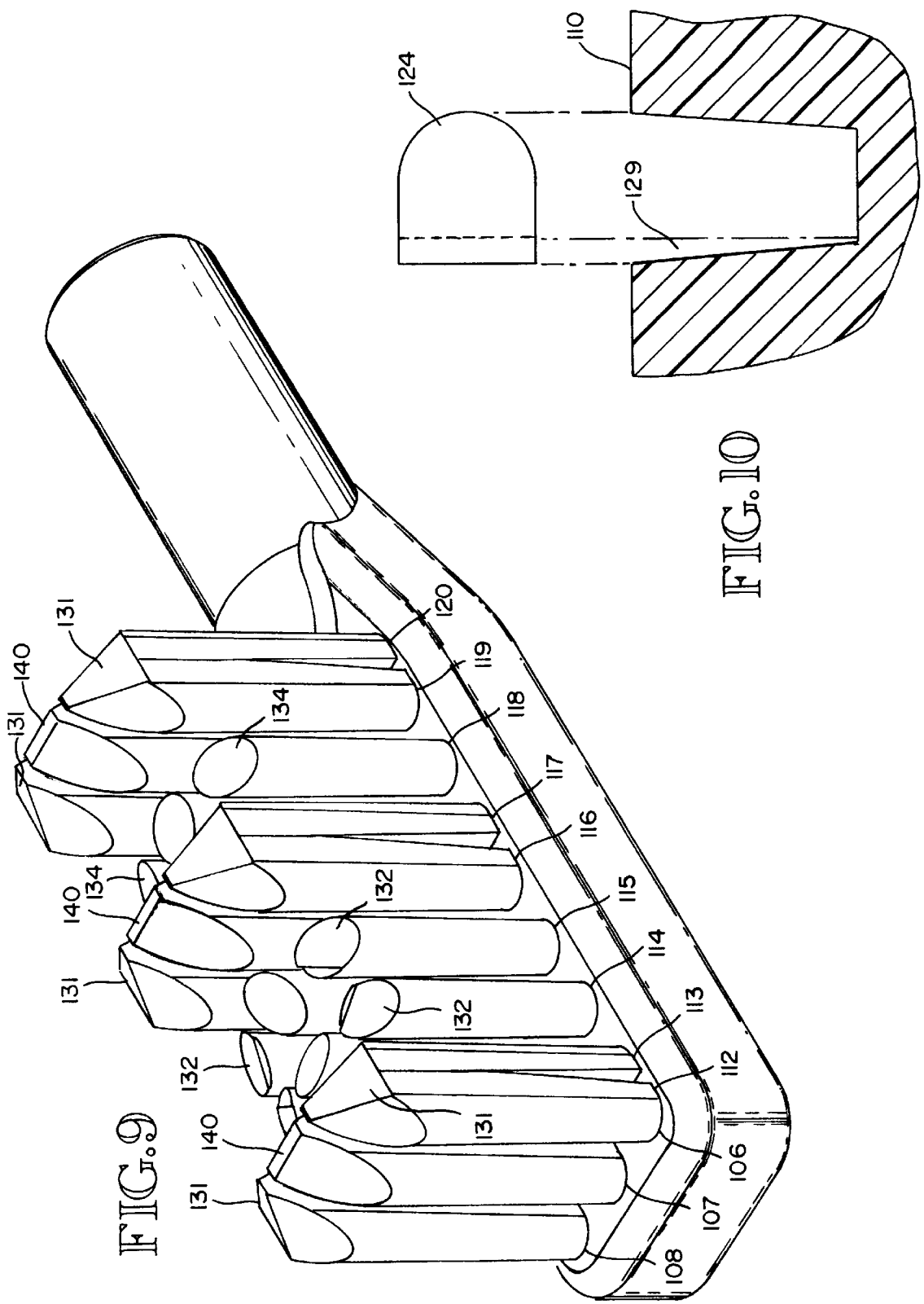

BRUSHHEAD FOR A TOOTHBRUSH

CROSS REFERENCE TO RELATED APPLICATION

This application is a continuation-in-part of patent application Ser. No. 09/150,877, filed Sep. 10, 1998.

TECHNICAL FIELD

This invention relates generally to acoustic (power) toothbrushes as well as manual toothbrushes, and more specifically concerns a particular brushhead configuration for use with such toothbrushes.

BACKGROUND OF THE INVENTION

Conventional toothbrush brushhead configurations tend to focus on the mechanical cleaning of the large, easily accessible buccal (exterior) and lingual (interior, adjacent the tongue) surfaces of the teeth. However, other areas of the dental region, including those teeth at the very rear of the mouth, and the interdental areas between the teeth, are more difficult to clean and are therefore often the site of dental disease. While there are some toothbrush brushhead configurations which are indicated to be effective for interdental regions, little improvement is typically experienced with such brushhead configurations. Hence, one significant issue with existing toothbrush configurations is the lack of effectiveness in difficult-to-reach areas. In some cases, interdental regions are reached beyond the tips of the bristles by the action of the toothbrush itself, such as with the toothbrush shown in U.S. Pat. No. 5,378,153, owned by the assignee of the present invention. However, even with such toothbrushes, it would be desirable to have a brushhead design which could give better coverage and/or penetration for the difficult-to-reach areas.

In addition to the problem of difficult-to-reach areas, many brushhead designs which are quite effective in removing plaque from teeth produce damage to the surrounding oral tissues which the bristles contact in the oral cavity. This is particularly true for power toothbrushes. Accordingly, it would be desirable for a brushhead to have a design which results in an enhanced cleansing effect in the difficult-to-reach areas, including the rear teeth surfaces and the interdental surfaces, but which also minimizes abrasion of the surrounding oral tissue.

DISCLOSURE OF THE INVENTION

Accordingly, the present invention is a brushhead for use with a toothbrush, either an electric powered toothbrush or a manual toothbrush, comprising: a base member for supporting a plurality of separate bristle tufts, wherein each tuft comprises a plurality of individual bristles; and a plurality of bristle tufts mounted in said base portion arranged in an array comprising nine rows and three columns, wherein the columns extend longitudinally of the base member and the rows extend laterally thereof, wherein from a distal end of the base member, first and second rows form a first set of tall bristle tufts, fifth and sixth rows form a second set of tall bristle tufts and eighth and ninth rows form a third set of tall bristle tufts, wherein each set of tall bristle tufts is approximately the same height and wherein the third, fourth and seventh rows are rows of bristle tufts which are relatively shorter than the tall bristle tufts.

BRIEF DESCRIPTION OF THE DRAWINGS

FIG. 9 is a perspective view of the brushhead of FIG. 8.

FIG. 10 is a cross-sectional view of a portion of the brushhead of FIG. 5.

BEST MODE FOR CARRYING OUT THE INVENTION

Figure 1:
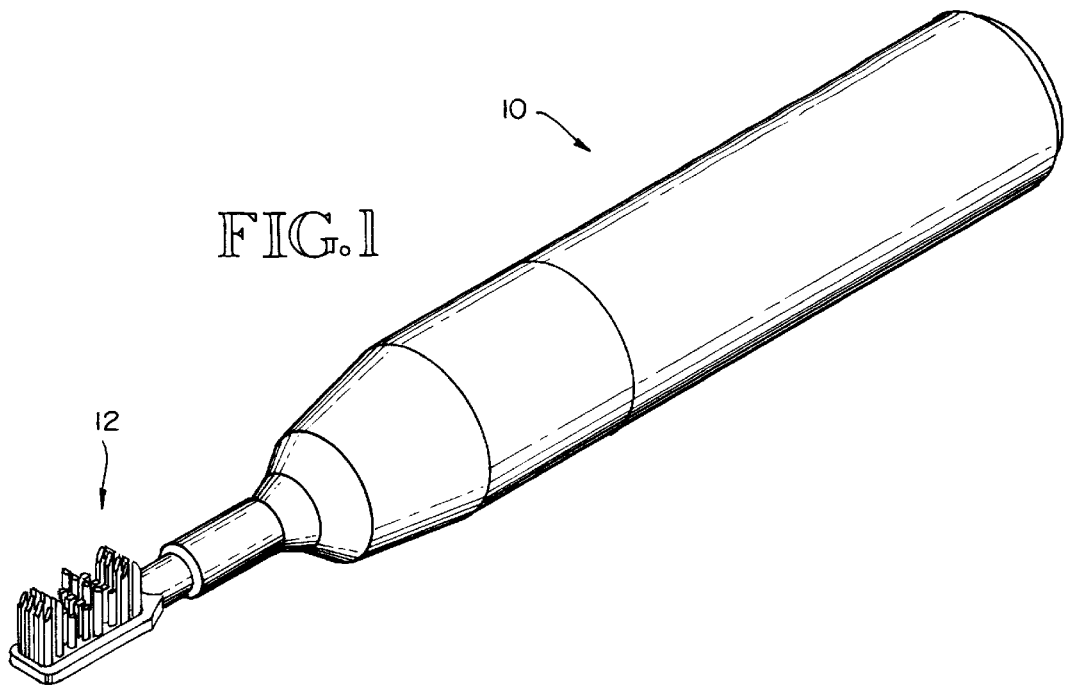
FIG. 1 is a perspective view of a power toothbrush with the brushhead configuration of the present invention.

FIG. 1 shows a power toothbrush generally at 10. The brushhead of the present invention, shown at 12, is positioned at the distal end of a lever arm portion of the power toothbrush. Toothbrush 10 operates with a brushhead frequency and amplitude which disrupts bacteria and removes plaque from the teeth of the user, including in the interdental regions, i.e. the regions between the teeth, and/or the subgingival regions between the gum and the teeth, as well as the hard-to-reach surfaces at the very rear of the mouth.

With the toothbrush shown, a fluid environment is maintained in the mouth so that the acoustic pressure created by movement of the brushhead within the mouth is coupled to the fluid in the interdental and subgingival regions of the teeth, while at the same time the sweeping action of the bristles mechanically removes plaque from the exposed areas of the teeth. While the brushhead 12 of the present invention is shown in the context of a particular power toothbrush, it should be understood that the brushhead could be used with a variety of power toothbrushes, particularly those within a certain frequency range, i.e. 150–400 Hz. A more precise operating frequency for the toothbrush is approximately 260 Hz.

Figure 2:
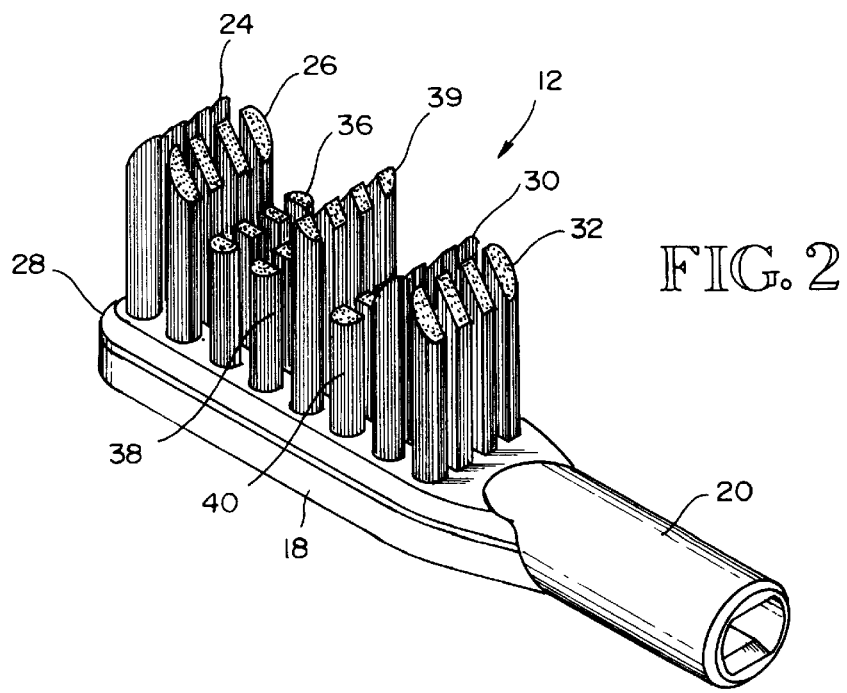
FIG. 2 is a perspective view of the brushhead shown in FIG. 1.
Figure 3:
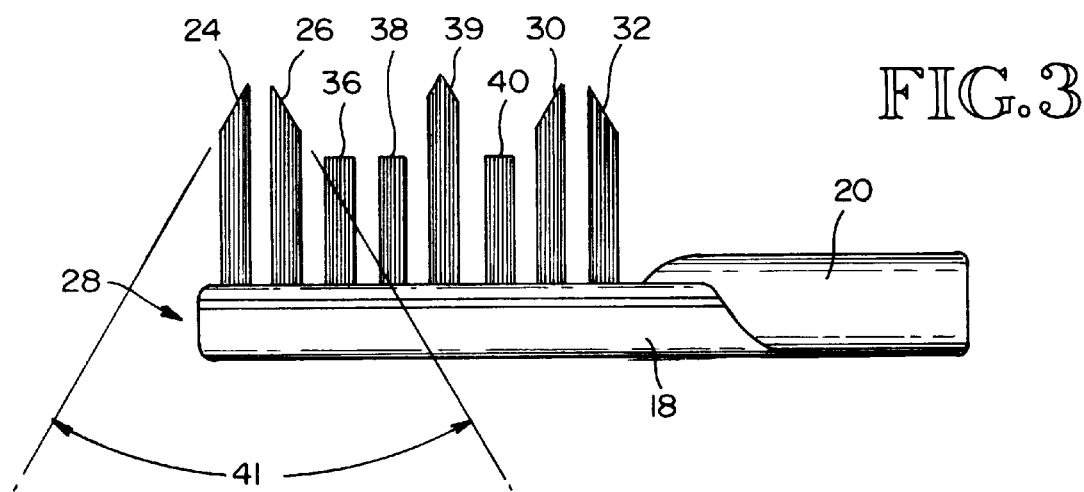
FIG. 3 is a side elevational view of the brushhead of FIG. 2.
Figure 4:
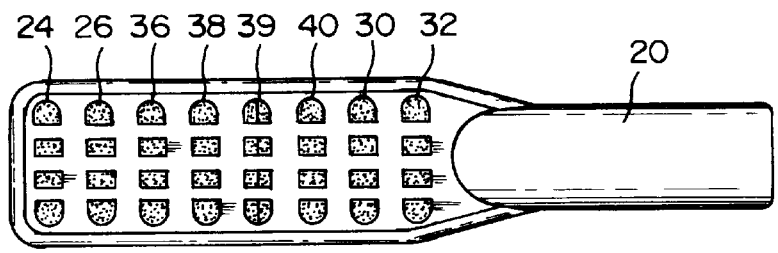
FIG. 4 is a top view of the brushhead of FIG. 2.

FIGS. 2, 3 and 4 show the brushhead arrangement of the present invention. Brushhead 12 includes a flat base portion 18. In the embodiment shown, base portion 18 is approximately 1.85 inches long by approximately 0.35 inches wide, and approximately 0.15 inches thick, with all dimensions being ±10%. At the proximal end of brushhead 12 is a connecting portion 20 which is hollow so it can receive a free end of a lever arm portion of the toothbrush.

The bristles on the brushhead are arranged in a pattern of four columns and eight rows of bristle groups in the embodiment shown with the columns extending longitudinally of the brushhead and the rows extending laterally thereof. In the embodiment shown, each bristle group comprises approximately 38±4 bristle strands, with the bristle strands in the embodiment shown being made from nylon, in one embodiment Dupont Tynex.

Using four columns instead of the conventional three results in a significant increase in bristle density. This increase in density, by increasing the total number of bristle strands, also known as tufts, in the same base area, produces both an improvement in the effect of the brushing and also, surprisingly, reduces abrasion; there is hence a reduction in harm to the oral tissue regions. Thus, the particular density of the individual bristle groups of the toothbrush are a significant aspect of the present invention. In the embodiment shown, the centerlines of the four columns are separated by approximately 0.07 inches and the centerlines of the rows are separated by approximately 0.1 inches.

In the embodiment shown, the brushhead has a particular arrangement of bristle strand or tuft lengths. Adjacent rows 24 and 26 at the distal end 28 of the brushhead are long bristles, having a total length from the base portion 18 of the brushhead of approximately 0.41 inches±0.01 inches. The two adjacent rows 30 and 32 at the proximal end of the brushhead are also long bristles, also having a maximum length of 0.41±0.01 inches.

Rows 36 and 38, which are two adjacent, successive rows of bristle portions inboard of distal rows 24 and 26 are both relatively short, approximately 0.26±0.01 inches long from base portion 18.

The next row of bristle portions inboard of row 38 is a single row 39 having a longest bristle strand length of 0.435 inches±0.02 inches. This row of bristle portions has bristle strands with a slightly smaller diameter than the bristle strands in the other bristle portions, in particular a 0.005 inch diameter as opposed to a 0.006 inch diameter. The combination of a single row with the bristle strands therein (1) being slightly longer than the long bristle strands of rows 24 and 26, (2) located approximately in the middle of the brushhead and (3) having a slightly smaller diameter than the other bristle strands, provides an increase in penetration of the bristles into, and a better fit for, the interdental region. Further, the extra long, small diameter bristles are less harmful to the gum tissue than conventional bristles.

The next row 40 of bristle portions is another short bristle length row, also approximately 0.26±0.01 inches long, similar to rows 36 and 38. Row 40 is located between the longest bristle length row 39 and the two rear proximal end rows 30 and 32. The total spacing between the distal long rows 24 and 26 and the central longest row 39 is designed to accommodate the posterior teeth, i.e. those teeth toward the rear of the mouth, while the total space between the longest row 39 and the proximal end long row 30 is designed to accommodate the anterior teeth, i.e. the teeth toward the front of the mouth. The short rows 36 and 38 brush against the sides of the posterior (molar) teeth, while the short row 40 brushes against the sides of the anterior teeth.

Hence, the overall brushhead configuration shown in FIGS. 2–4 tends to more accurately accommodate the actual arrangement and various sizes of the teeth in the mouth, so as to provide better and more uniform bristle coverage for the teeth and hence better cleansing action. The bristle portions of the embodiment shown as a unit thus better fits the variety of teeth sizes actually present in the human mouth.

The short bristle rows 36, 38 and 40 all have flat tops, although each individual bristle strand is rounded. On the other hand, the long distal end rows 24 and 26, the long proximal end rows 30 and 32, and the intermediate longest row 39 all have angled bristle portions, as shown in FIGS. 2 and 3, even though each individual bristle strand is rounded, as indicated above. The distal end long row pair and the proximal end long row pair angle to a point, while longest row 39 is itself configured to a point. The bristle angle 41 (shown in FIG. 3) is within the range of 56° to 72°. It has been discovered that this range of angle is actually quite significant in improving the effects of the brush. The range of angle improves plaque removal on all the teeth, and especially improves interdental cleaning.

Figure 5:
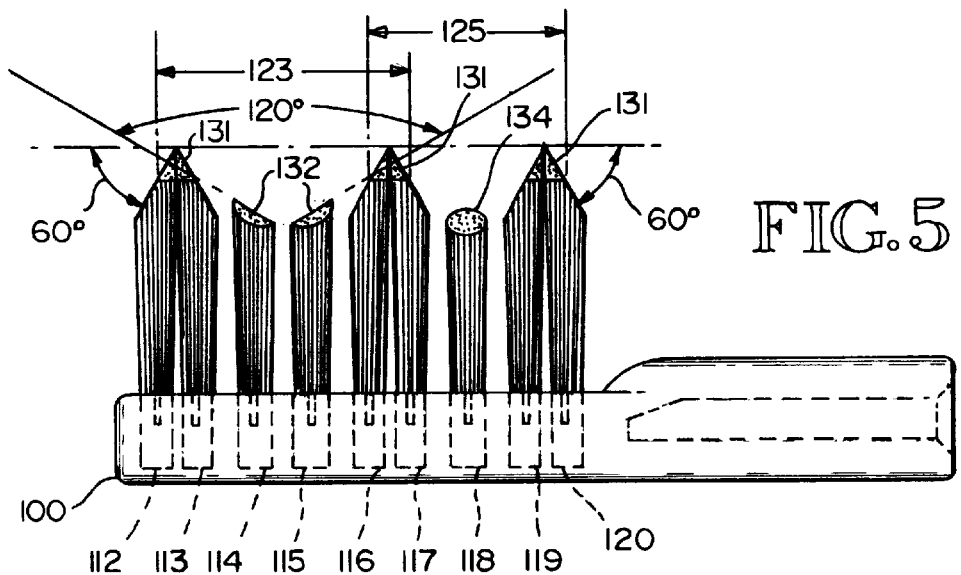
FIG. 5 is a side elevational view of another embodiment of an improved brushhead.
Figure 7:
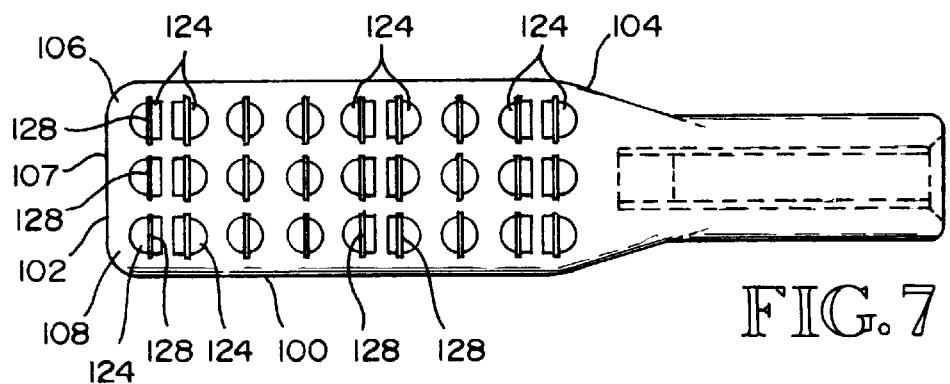
FIG. 7 is a top view of the base member portion of the brushhead of FIG. 5.
Figure 6:
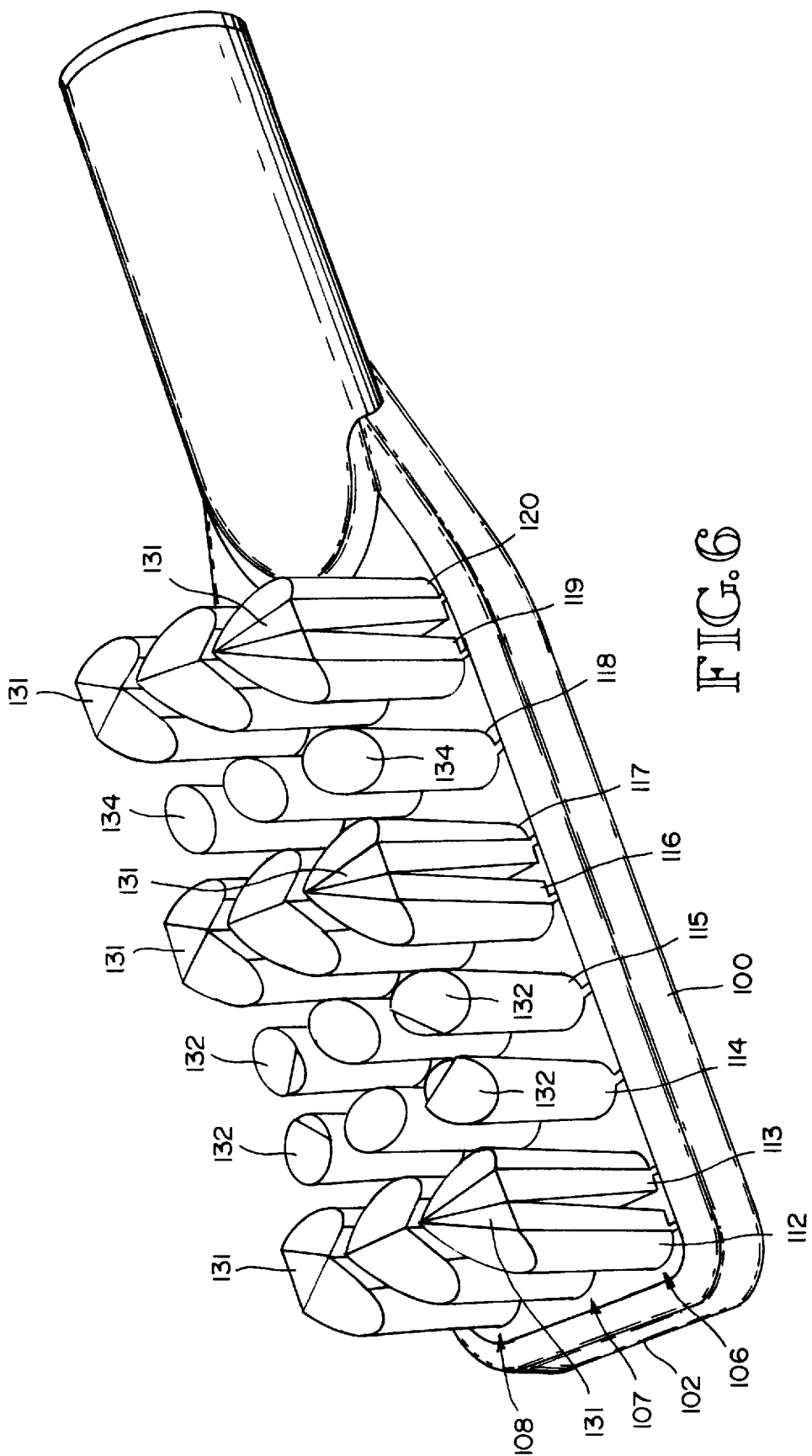
FIG. 6 is a perspective view of the brushhead of FIG. 5.

FIGS. 5–10 show additional embodiments of brushhead designs. These brushheads can be used in a power toothbrush or a manual toothbrush. These embodiments provide good interdental cleaning as well as good cleaning along the edges of adjacent teeth and along the gum line. The spacing and configuration of the bristle tufts are optimized to match the interdental spacing of a typical mouth, as described in more detail below. FIGS. 5–7 show one of the additional embodiments. This embodiment includes a brushhead base member 100 similar in configuration and size to the brushhead base member of the previous embodiments. Basically, the base member 100 has approximate dimensions as follows: 0.35 inches wide by 0.15 inches thick and 0.84 inches long from a distal end 102 to the point where the base member begins to decrease in width at 104. These dimensions could be varied.

In the embodiment shown, the bristles are arranged into columns and rows of bristle (filament) groups, referred to as tufts. In the particular embodiment shown, there are three bristle tuft columns 106, 107 and 108, which extend longitudinally of the base member, and nine bristle tuft rows 112–120, which extend laterally of the base member. Rows 112, 113, 116, 117, 119 and 120 are all tall bristle tufts, with the individual bristles having a diameter of 0.006 inches (with a possible range of 0.003–0.007 inches), while rows 114, 115 and 118 are shorter bristle tufts, the individual bristles having a diameter of 0.005 inches (with a possible range of 0.003–0.007 inches). However, bristles in the shorter rows 114, 115 and 118 will have a smaller diameter than the tall bristles so that they have the same "soft" feel and flexibility to the user as the taller bristle rows while still providing good cleansing action for the teeth adjacent the gum line with only minimal, if any, abrasion effect on the gums and/or teeth.

The bristle (filament) tufts in tall bristle rows 112, 113, 116, 117, 119 and 120 are inserted into D-shaped openings 124—124, with the tufts in adjacent rows (112 and 113, 116 and 117, and 119 and 120) having the flat side of the D-shaped openings facing each other, as shown most clearly in FIG. 7. The D-shaped openings are approximately 0.020 inches apart in the embodiment shown. The actual shape of the "D" could be somewhat oblong or oval. The bristle tufts in the shorter bristle rows 114, 115 and 118 are positioned in openings having a circular cross-section, although this shape could be varied including oval or oblong. The bristle tufts are inserted into the D-shaped openings 124—124 around solid staples 128—128. Each staple 128 is a rectangle, approximately 0.08 inches long and 0.06 inches wide and 0.01 inches thick, in one example. Other staple sizes and configurations of staples could be used. The plurality of individual bristles, in accordance with standard practice, are looped around the lower edge of the staple. The total length of each bristle is somewhat more than twice the length of the height of the bristles from the base member. The staple is inserted into the opening, with the loop bristles, to form a bristle tuft. The bristles could also be molded into the base member.

The staples 128—128 are oriented at 90° to the longitudinal axis of the brushhead, i.e. laterally of the brushhead. This is quite different than traditional arrangements, in which the staples are oriented either along the longitudinal axis or at a relatively small angle (e.g. 15°) relative to the longitudinal axis. The orientation of the staple in the embodiment shown permits adjacent tufts in a given column to be positioned closer to each other than otherwise, which provides advantages in brushing. The adjacent bristle tufts in any column for rows 112, 113 and 116, 117 and 119, 120 are referred to as bristle tuft pairs.

Also, the flat side of each D-shaped opening 124 is tapered slightly outwardly from the bottom to the top thereof, so that the individual bristles near the flat side of the D-shaped opening in each bristle pair tend to lean toward each other and to contact and intermingle slightly at the very top thereof. More bristles are present in a given area with the use of the staple orientation and the D-shaped opening arrangement. The angled shape of the D-shaped opening is referred to as a "draft" and is shown in FIG. 10 at 129. This is in addition to any small angle (e.g. 1°) which may be present around the entire opening, such as to facilitate manufacture of the base member. This results in a denser brush at the very tops of the bristle pairs, which in turn results in more bristles in the peak area of the bristle pairs and more bristles actually coming into contact with the teeth and the interdental area. This is quite effective in producing a good cleansing effect on and between the teeth. The additional draft angle at the flat side of the D-shaped opening is quite small, in the range of 1–10°, preferably approximately 1–2°. The preferred range is applicable when the spacing between the D-shaped openings is approximately 0.020 inches.

The result of this arrangement is shown most clearly in FIG. 5, in which the bristles near the flat side of the D-shaped openings of each bristle pair (rows 112, 113 and 116, 117 and 119, 120 for each column) lean toward each other slightly, resulting in contact and a slight intermingling at the top of each bristle pairs. More specifically, with a 0° draft, there will typically be a slight opening at the top of the bristle pairs. With a 1° draft, there will be an intermingling part of the way down the bristles. A 2° draft will result in an intermingling beginning at slightly less than half the height of the bristles, FIG. 5 shows a 1° draft. Again, this is with a D-shaped opening spacing of 0.020 inches.

The spacing of the bristles is shown in FIG. 5. The distance between the centerline between tall bristle rows 112 and 113 and tall bristle rows 116 and 117 is, in the embodiment shown, within a range of 0.350–0.45 inches, preferably approximately 0.388 inches, while the distance between the centerline between tall bristle rows 116 and 117 and tall bristle rows 119 and 120 is within a range of 0.20–0.30 inches, preferably approximately 0.287 inches. For the preferred spacing, the midbevel distance 123 is approximately 0.46 inches, while midbevel distance 125 is approximately 0.36 inches. The bevel configuration of the tops of the bristles is discussed in more detail below. The short bristle rows, i.e. rows 114, 115 and 118, are spaced equally between the adjacent tall bristle rows.

The spacing of the rows and the arrangement of the tall bristle tufts are optimized to match the interdental distances of typical mouth anatomy. The 0.388 inch distance is designed to accommodate the interdental spacing of teeth toward the rear of the mouth (the molars) and the upper incisors. The 0.287 inch distance is designed for the spacing of teeth toward the front of the mouth (excluding the upper incisors).

The spacing is particularly advantageous when the toothbrush moves in an up/down manner against the teeth (as opposed to an in/out, i.e. back and forth manner). The up/down manner is preferred by a majority of dentists.

The tall bristle tufts are designed to produce effective cleansing action between the teeth and along the vertical edges of the teeth adjacent the interdental region. The shorter bristle tufts are of a length which results in a gentle cleaning action of the exposed surfaces of the teeth and the gum line.

FIGS. 5 and 6 show the particular configuration of the tops of the bristles, which is important for effective cleansing action. The configuration of the bristle tops has several characteristics. The first characteristic is that the tops of the bristles in the tall bristle pairs are trimmed at an angle to a point, 60°±5° from the horizontal. Hence, the included angle of the bristles in the tall bristle (filament) pairs is also 60°. The angle from the horizontal could be in the range of 40°–65°. Further, the outer side surface of the taller bristle tufts (rows 112, 113, 116, 117, 119 and 120) are beveled inwardly at 131 at the top portion thereof. In the embodiment shown, this angle is 37°±5°, but could be within a range of 20°–50°. This beveled arrangement is shown most clearly in FIG. 6. This particular structure of the tall bristle pairs promotes effective cleansing action in the interdental spaces between the teeth and the vertical edges of the teeth, where adjacent teeth come close to or actually contact each other.

In each column of shorter rows 114 and 115, the tops of the bristle tufts are trimmed downwardly toward each other at an angle of 60° from the horizontal, for a total included angle between bristle tufts in rows 114 and 115 in each column of 120°±5°, as shown most clearly in FIG. 5. This angle could, however, be in a range of 60°–134°. In addition, the outside edge of bristle tufts in columns 106 and 108, rows 114 and 115 are beveled inwardly at 132 at the top portion of the bristle tuft. In the embodiment shown, the angle is 30°±5°. This angle can, however, be within a range of 20°–50°. Beveled portion 132 of each bristle tuft intersects the angled portion at the top thereof, producing a complex top surface for the tufts in columns 106 and 108, rows 114 and 115.

In row 118, the top surface of the bristle tuft in the middle column (column 107) is flat, while the bristle tufts in columns 106 and 108 are both beveled inwardly at 134 at the outside edge thereof, at the top portion of the bristle tufts. In the embodiment shown, the angle is 30°±5°, although this angle can be within a range of 20°–50°.

The beveled portion at the outside edges of the tall bristle tufts in columns 106 and 108 is particularly effective in cleaning action when the brushhead is held at an angle with the range of 20°–40° during brushing. The midbevel distance also promotes effective cleaning.

In the embodiment shown, the peak of each of the tall bristle pairs (rows 112, 113 and 116, 117 and 119, 120) is 0.43 inches. The height of the bristle tufts in rows 114 and 115 is approximately 0.34 inches adjacent the tall bristle tufts in rows 113 and 116, respectively, while the height of those tufts at their opposing edges is approximately 0.296 inches. This is due to the angled top surface of those bristle tufts. The height of the entire bristle tuft in row 118, column 107 is 0.32 inches. In row 118 columns 106 and 108, beveled portions 134 of those tufts extend downwardly from that height to the outside edge surface of the bristle tufts. The peak of the tall bristles is within a range of 0.39–0.45 inches, with 0.43 inches preferred, while the peak of the shorter bristles is 0.26–0.36 inches, with 0.32 preferred as an average peak value.

The above-described particular brush configuration has been found to provide significantly improved plaque-removing capability, including surprising improvement even over the improved brush designs of FIGS. 1–4. This is the result of the combination of several of the above specific features. The tall pairs of bristles provide good interdental and edge surface cleansing, while the shorter bristles provide good cleansing along the surfaces of the teeth as well as along the gum line, without producing abrasion of the teeth. Further, this particular configuration of brushhead may be used on manual toothbrushes, as well as power toothbrushes.

Figure 8:
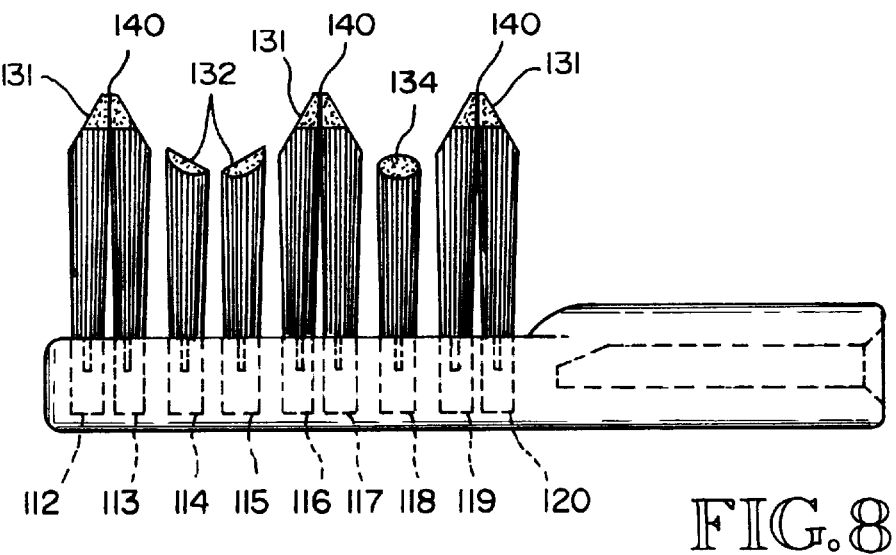
FIG. 8 is a side elevational view of a modification of the brushhead of FIG. 5.

FIGS. 8 and 9 show a similar embodiment with similar brush configuration and arrangement to that shown in FIGS. 5–7, with the exception that the very tops of the tall bristle pairs, i.e. those bristle pairs in rows 112, 113, 116, 117, 119 and 120 are rounded or flattened at the top 140 instead of coming to a point (i.e. a narrow line across the brushhead). The width of the flat section is in the embodiment shown approximately 0.02 inches, although this could be varied somewhat.

Hence, a new brushhead configuration for a power or manual toothbrush has been described which incorporates several specific improvements, resulting in improved performance and cleansing, while decreasing abrasion.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. A brushhead for use with a toothbrush, comprising:
   a base member for supporting separate bristle tufts, each tuft comprising a plurality of bristles; and
   a plurality of bristle tufts mounted in said base member, arranged in an array comprising nine rows and three columns, wherein the columns extend longitudinally of the base member and the rows extend laterally thereof, wherein from a distal end of the base member, first and second rows form a first set of tall bristle tufts, fifth and sixth rows form a second set of tall bristle tufts, and eighth and ninth rows form a third set of tall bristle tufts, wherein each set of tall bristle tufts are approximately the same height, and wherein third, fourth and seventh rows are rows of bristle tufts which are relatively shorter than the tall bristle tufts.

2. An article of claim 1, wherein the first, second and third sets of tall bristles are angled to a narrow line at the top ends thereof laterally of the base member.

3. An article of claim 2, wherein the angle is within the range of 40°–80°.

4. An article of claim 3, wherein the angle is 60°±5°.

5. An article of claim 2, wherein the top of each set of tall bristles is flat, approximately 0.02 inches wide.

6. An article of claim 2, wherein the tall bristle tufts in each row, respectively, of tall bristle tuft pairs in the first, second and third sets of tall bristles are slightly angled toward each other so that they contact and intermingle at the top thereof.

7. An article of claim 6, wherein the tall bristle tufts are set close enough together that the angle of inclination is within the range of 1–2°.

8. An article of claim 2, wherein the shorter bristle tufts in the third and fourth rows of all three columns have top surfaces which have been initially trimmed to angle downwardly toward each other.

9. An article of claim 8, wherein the trim angle is within the range of 60°–134°.

10. An article of claim 9, wherein the trim angle is 120°±5°.

11. An article of claim 8, wherein the shorter bristle tufts in the third and fourth rows of the first and third columns have been further trimmed to bevel inwardly along an outer edge surface thereof at an upper end portion thereof.

12. An article of claim 11, wherein the bevel is within a range of 20°–50°.

13. An article of claim 12, wherein the bevel is 30°±5°.

14. An article of claim 2, wherein the shorter bristle tuft of the second column, seventh row, has a flat top, and wherein the bristle tufts of the first and third columns, seventh row, have been trimmed to bevel inwardly along an outer edge surface thereof at an upper end portion thereof.

15. An article of claim 14, wherein the bevel is within a range of 20°–50°.

16. An article of claim 15, wherein the bevel is 30°±5°.

17. An article of claim 2, wherein the rows of bristle tufts are spaced in accordance with typical interdental distances.

18. An article of claim 1, wherein the third and fourth rows are approximately evenly spaced between the first and second sets of tall bristle tufts, and wherein the seventh row is approximately evenly spaced between the second and third sets of tall bristle tufts.

19. An article of claim 18, wherein the bristle tufts in the first and third columns of the first, second and third sets of tall bristles are beveled inwardly along an outer edge surface thereof at an upper end portion of the bristle tufts.

20. An article of claim 19, wherein the bevel is within the range of 20°–50°.

21. An article of claim 20, wherein the bevel is 37°±5°.

22. An article of claim 19, wherein the shorter bristles have a height which extends above a lower edge of the bevel on the tall bristle tufts.

23. An article of claim 1, wherein the tall bristle tufts in each row, respectively, of tall bristle tuft pairs in the first, second and third sets of tall bristles are slightly angled toward each other so that they contact and intermingle at the top thereof.

24. An article of claim 1, wherein the bristles in the first, second and third set of tall bristle tufts have a diameter within the range of 0.003–0.007 inches, while the bristles in the shorter bristle tufts have a diameter of approximately within the range of 0.003–0.007 inches, with the shorter bristles having a diameter less than the tall bristles, so that the tall and short bristles feel approximately the same to a user.

25. An article of claim 24, wherein the diameter of the tall bristles is approximately 0.006 inches while the diameter of the shorter bristles is approximately 0.005 inches.

26. An article of claim 1, wherein the bristle tufts are held in the base member by relatively thin staple members, and wherein such staple members are oriented laterally of the base member.

27. An article of claim 1, wherein openings in the base member for the bristle tufts are approximately circular in cross-section for the third, fourth and seventh rows, while the openings in the base member for the bristle tufts are approximately D-shaped in cross-section for the first, second, fifth, sixth, eighth and ninth rows, wherein flat portions of the D-shaped openings face each other for the first and second, fifth and sixth, and eighth and ninth rows, permitting the bristle tufts in those rows to be spaced closer together than otherwise.

28. An article of claim 1, wherein the toothbrush is a manual toothbrush.

29. An article of claim 1, wherein the toothbrush is an electric toothbrush.

30. A brushhead for use with a toothbrush, comprising:
   a base member for supporting separate bristle tufts in an array of columns and rows, wherein the columns extend longitudinally of the base member and the rows extend laterally thereof, the rows of bristle tufts at the opposing ends of the base member and intermediate thereof are tall compared with rows of shorter bristle tufts positioned therebetween, wherein the short bristles have a smaller diameter than the taller bristles, wherein the tall bristles are angled to approximately a narrow line at the top ends thereof, laterally of the base member, and wherein the taller bristles in the outermost columns are beveled inwardly along an outer edge surface at an upper end thereof and wherein the shorter bristles are beveled inwardly along an outer edge surface thereof at an upper end thereof.

31. An article of claim 30, wherein the taller bristles have a diameter of 0.006 inches and the shorter bristles have a diameter of 0.005 inches.

32. An article of claim 30, wherein the tall bristle angle is within the range of 40°–60°, the bevel for the tall bristles is within the range of 20°–50° and wherein the bevel for the shorter bristles is within the range of 20°–50.

33. An article of claim 32, wherein the tall bristle angle is approximately 60°, and wherein the bevel for the taller bristles is approximately 37° and the bevel for the shorter bristles is approximately 30°.

34. An article of claim 30, wherein the taller bristles are angled slightly toward each other so that they contact and intermingle at their respective top portions thereof.

35. An article of claim 30, wherein the bristles are held into openings in the base member by relatively thin staple members, and wherein the staple members are oriented laterally of the base member.

36. An article of claim 30, wherein the shorter bristles are equally spaced between the adjacent tall bristles.

37. An article of claim 30, wherein the toothbrush is a manual toothbrush.

38. An article of claim 30, wherein the toothbrush is an electric toothbrush.

39. A brushhead for use with a toothbrush, comprising:

a base member for supporting separate bristle tufts in an array of columns and rows, wherein the columns extend longitudinally of the base member and the rows extend laterally thereof, wherein the rows of bristle tufts located in tall bristle regions at the opposing ends of the base member and intermediate thereof are tall compared with the rows of shorter bristle tufts positioned therebetween, wherein the bristle tufts in the tall bristle regions are trimmed to a narrow top which extends laterally of the base member and wherein at least some of the tall bristles in each of the tall bristle regions are positioned so that they angle toward each other, intermingling at the top portions thereof, wherein each tall bristle region includes back-to-back D-shaped openings for holding bristle tufts and wherein the bristle tufts are held in the openings by staples which extend laterally of the base member.

40. A brushhead of claim 39, wherein flat sides of the D-shaped openings, are angled outwardly within a range of 1°–2° and wherein the back-to-back D-shaped openings are separated by approximately 0.020 inches.

* * * * *